(12) United States Patent
Ziehl et al.

(10) Patent No.: US 10,156,550 B2
(45) Date of Patent: Dec. 18, 2018

(54) NON-INTRUSIVE METHODS FOR THE DETECTION AND CLASSIFICATION OF ALKALI-SILICA REACTION IN CONCRETE STRUCTURES

(71) Applicant: University of South Carolina, Columbia, SC (US)

(72) Inventors: Paul Henry Ziehl, Irmo, SC (US); Mohamed K. ElBatanouny, Columbia, SC (US); Matthew K Jones, Columbia, SC (US)

(73) Assignee: University of South Carolina, Columbia, SC (US)

( * ) Notice: Subject to any disclaimer, the term of this patent is extended or adjusted under 35 U.S.C. 154(b) by 276 days.

(21) Appl. No.: 14/949,009

(22) Filed: Nov. 23, 2015

(65) Prior Publication Data
US 2016/0209372 A1  Jul. 21, 2016

Related U.S. Application Data

(60) Provisional application No. 62/082,752, filed on Nov. 21, 2014.

(51) Int. Cl.
*G01N 29/14* (2006.01)
*G01N 33/38* (2006.01)
*G01N 29/46* (2006.01)

(52) U.S. Cl.
CPC ............. *G01N 29/14* (2013.01); *G01N 29/46* (2013.01); *G01N 33/383* (2013.01); *G01N 2291/0232* (2013.01); *G01N 2291/0255* (2013.01)

(58) Field of Classification Search
CPC ........ G01N 29/14; G01N 29/00; G01N 29/04; G01N 29/041; G01N 29/046; G01N 29/11;
(Continued)

(56) References Cited

U.S. PATENT DOCUMENTS 5,010,503 A * 4/1991 Paton .................... G01N 29/14
                                                            702/176
5,109,195 A * 4/1992 Allison ................ G01N 27/725
                                                            324/209

(Continued)

OTHER PUBLICATIONS

Rivard et al. ("Assessing alkali-silica reaction damage to concrete with non-destructive methods: From the lab to the field," Construction and Building Materials, pp. 902-909, Jun. 16, 2008, Department of Civil Engineering, Universite de Sherbrooke, Canada J1K 2R1).*

(Continued)

*Primary Examiner* — Max Noori
(74) *Attorney, Agent, or Firm* — Dority & Manning, P.A.

(57) ABSTRACT

Methods of using acoustic emission (AE) as a condition assessment technique for alkali-silica reaction (ASR) in concrete are provided. ASR is a chemical reaction occurring between alkaline hydroxides within cement past and certain types of amorphous silica found in mineral aggregates. ASR causes an accumulation of internal pressure due to the formation of a hygroscopic gel which leads to expansion and cracking of the concrete. AE is highly sensitive to stress waves emitted from a sudden release of energy such as formation of cracks in concrete. This allows it to capture and identify propagating damage. AE has the potential to detect micro-cracks forming prior to expansion, which can be related to the degree of ASR damage.

10 Claims, 9 Drawing Sheets

(58) Field of Classification Search
CPC ...... G01N 29/12; G01N 29/265; G01N 29/36; G01N 29/44; G01N 29/46; G01N 33/383; G01N 2291/0232; G01N 2291/0255; G01N 2291/0231; G01N 2291/263; G01N 2291/2698
USPC .......................................................... 73/587
See application file for complete search history.

(56) References Cited

U.S. PATENT DOCUMENTS

| | | | | |
|---|---|---|---|---|
| 5,293,555 | A * | 3/1994 | Anthony | G01M 5/0033 702/36 |
| 5,739,035 | A * | 4/1998 | Guthrie, Jr. | G01N 31/22 436/164 |
| 5,798,457 | A * | 8/1998 | Paulson | E04C 5/08 73/587 |
| 5,928,420 | A * | 7/1999 | Oates | C04B 28/02 106/705 |
| 6,170,334 | B1 * | 1/2001 | Paulson | E04C 5/08 73/587 |
| 9,678,045 | B2 * | 6/2017 | Zhu | G01N 29/34 |
| 2004/0025593 | A1 * | 2/2004 | Hashimoto | G01N 17/006 73/643 |
| 2005/0172697 | A1 * | 8/2005 | Nozaki | G01M 3/005 73/12.01 |
| 2009/0116533 | A1 * | 5/2009 | O'Connell | G01N 25/72 374/5 |
| 2011/0172982 | A1 * | 7/2011 | Veeraraghavan | G01N 21/9501 703/13 |
| 2015/0338380 | A1 * | 11/2015 | Ziehl | G01N 29/14 73/587 |

OTHER PUBLICATIONS

Naffa et al. ("Detection of chemical damage in concrete using ultrasound," Ultrasonics 40 (2002), pp. 247-251, 2002 Electronics and Acoustics Group, France).*
Deroo et al. ("Detection of damage in concrete using diffuse ultrasound (L)," J. Acoust. Soc. Am. Mar. 31, 2010, pp. 3315-3318, The Journal of the Acoustical Society of America.*
Assouli, B., Simescu, F., Debicki, G., and Idrissi H. 2005. Detection and identification of concrete cracking during corrosion of reinforced concrete by acoustic emission coupled to the electrochemical techniques. NDT & E International, 38(8), 682-689.
ASTM C 1260-07. 2007. Potential Alkali Reactivity of Aggregate (Mortar-Bar Method). American Society for Testing Materials, Philadelphia, 652-655.
ASTM C114-13. 2013. Standard Test Methods for Chemical Analysis of Hydraulic Cement. American Society for Testing and Materials, 1-16.
ASTM C1293. 2008. Standard Test Method for Determination of Length Change of Concrete Due to Alkali-Silica Reaction. American Standard for Testing and Materials, 1-7.
ASTM C138 / C138M-13a. 2013. Standard Test Method for Density (Unit Weight), Yield, and Air Content (Gravimetric) of Concrete. American Society for Testing and Materials, 1-9.
ASTM C157 / C157M-08. 2008. Standard Test Method for Length Change of Hardened Hydraulic-Cement Mortar and Concrete. American Society for Testing and Materials, 1-5.
ASTM C192 / C192M-13a, 2013, Standard Practice for Making and Curing Concrete Test Specimens in the Laboratory. American Society for Testing and Materials, 7-20.
ASTM C231 / C231M-10. 2010. Standard Test Method for Air Content of Freshly Mixed Concrete by the Pressure Method. American Society for Testing and Materials, 1-9.
ASTM C29 / C29M-09. 2009. Standard Test Method for Bulk Density ("Unit Weight") and Voids in Aggregate. American Society for Testing and Materials, 1-13.
ASTM E1316. 2006. Standard Terminology for Nondestructive Examinations. American 161 Society for Testing and Materials, 1-33.
ElBatanouny, M., Mangual, J., Ziehl, P., and Matta, F. 2011, Corrosion Intensity Classification in Prestressed Concrete using Acoustic Emission Technique. Proc. American Society for Nondestructive Testing (ASNT) Fall Conference and Quality Testing Show 2011, Palm Springs, CA. Oct. 24-28, 10.
ElBatanouny, M.K. Larosche, A., Mazzoleni, P., Ziehl, P.H, Matta, F., and Zappa, E. 2012. Identification of Cracking Mechanisms in Scaled FRP Reinforced Concrete Beams using Acoustic Emission. Experimental Mechanics, DOI 10.1007/s11340-012-9692-3, November (online).
Fowler, T., Blessing, J., and Conlisk, P. 1989. New Directions in Testing. Proc. $3^{rd}$ International Symposium on AE from Composite Materials. Paris, France.
Idrissi, H., and Limam, A. 2003. Study and characterization by acoustic emission and electrochemical measurements of concrete deterioration caused by reinforcement steel corrosion. NDT & E International, 36(8), 563-569.
Mangual, J., ElBatanouny, M. K., Ziehl, R, and Matta, F. 2013. Acoustic-Emission-Based Characterization of Corrosion Damage in Cracked Concrete with Prestressing Strand. ACI Materials Journal, 110(1), 89.
Pollock, A.A. 1986. Classical Wave Theory in Practical AE Testing. Progress in AE III, Proceedings of the 8th International AE Symposium, Japanese Society for Nondestructive Testing, 708-721.
Swamy, R.N. 1998: The Alkali-Silica Reaction in Concrete, New York, Blackie and Son Ltd.
Ziehl, P. 2008. Applications of Acoustic Emission Evaluation for Civil Infrastructure. SPIE Proc. SPIE Smart Structures NDE, San Diego, CA, 9.

* cited by examiner

NON-INTRUSIVE METHODS FOR THE DETECTION AND CLASSIFICATION OF ALKALI-SILICA REACTION IN CONCRETE STRUCTURES

PRIORITY INFORMATION

The present application claims priority to U.S. Provisional Patent Application Ser. No. 62/082,752 titled "Non-Intrusive Methods for the Detection and Classification of Alkali-Silica Reaction in Concrete Structures" of Ziehl, et al. filed on Nov. 21, 2014, the disclosure of which is incorporated by reference herein.

BACKGROUND

Introduction to ASR in Concrete

Concrete is widely used around the world for the construction of many infrastructure including highway bridges, residential and commercial building, dams, electric power generation plants, and nuclear power plants. The heterogeneous nature of concrete makes it susceptible to various deterioration mechanisms including corrosion of reinforcement, sulfate attack, alkali-aggregate reaction (AAR), freeze-thaw cycling, leaching, radiation, elevated temperatures, salt crystallization, and microbiological attack. Concrete deterioration may jeopardize the serviceability and safety of structures leading to economic losses and ultimately catastrophic failures and fatalities. It is, therefore, necessary to evaluate the condition of aging concrete structures in order to predict their remaining service life.

The presence of cracks from alkali-silica reaction (ASR) at the Seabrook Nuclear Power Plant (NRC 2011) has brought this type of deterioration of reinforced concrete to the attention of the general public. ASR is a mechanism that depends on material selection of the concrete matrix and permits few mitigation techniques once the structure is in-service. This prompted the U.S. Nuclear Regulatory Commission (NRC) to issue a nationwide warning to all NPPs operators.

Currently the most prevalent means of preventing ASR is proper selection of materials. Most commonly a potential aggregate is screened for ASR subjectivity using laboratory testing procedures. It is noted that the concrete used in the Seabrook Nuclear Power Plant was examined using ASTM C289 and ASTM C295, which are the standards used at the time of construction to detect ASR, yet ASR degradation still occurred. The ASTM C1293 and the ASTM C1260 are the two most popular test methods being used today to evaluate the potential of an aggregate to participate in expansive ASR. Although these methods show a much improved ability to identify aggregates subject to ASR than previous test method, each has limitations. Both the ASTM C1293 and the ASTM C1260 have been shown to falsely identify aggregates as innocuous and conversely reject certain aggregates which have shown satisfactory field performance. It is for this reason that even careful material selection cannot completely eliminate the incidence of deleterious ASR in the field.

ASR initiates when certain types of reactive siliceous aggregates are combined with cement alkaline hydroxides originating from Portland cement. The mechanism requires as little as 80-percent relative humidity to occur. The reaction product is a gelatinous material that swells when moisture is absorbed and can cause expansion and cracking in concrete structures.

Regular inspections are needed to determine the extent and rate of ASR deterioration. This can be achieved through examination of concrete cores to determine the mechanical properties of concrete as well as in-situ monitoring through crack mapping. However, visual inspection gives only information related to the surface condition of concrete. Therefore, there is a need for an efficient non-destructive testing (NDT) method to monitor the progression of ASR. The NDT technique should enable (1) proper assessment of the rate of ASR deterioration and (2) evaluate the remaining service life.

There are several popular testing methods for evaluating the potential of aggregates for ASR reactivity.

The ASTM C295 test method is used to determine the physical and mineralogical characteristics of aggregates. Typically the petrographic examination requires the use of optical microscopy to classify different rock types and mineral constituents within an aggregate. Identifying constituents of an aggregate is generally a necessary step in determining the properties that may be expected to influence behavior, such as ASR subjectivity, during intended use. Because potentially deleterious minerals such as reactive silica present in an aggregate can be identified using petrographic examination it is commonly used as a criterion in the proper selection of materials in order to prevent ASR. However petrography is limited in that certain types of slowly-reactive minerals such as microcrystalline, strained, or microfractured quartz cannot be clearly identified and these minerals are commonly occurring in a wide variety of aggregates. Another drawback to the C295 is that the interpretation of results can vary widely depending on the petrographers experience level and background.

The ASTM C227 is a test method that is used to determine the susceptibility of cement-aggregate combinations to expansive alkali-aggregate reactions including ASR. This test has been proven as inadequate in identifying certain slowly reactive aggregates such as greywackes and argillites (Bérubé and Fournier 1992). Storage containers containing wicks have been shown to cause leaching of alkalis from mortar bars causing seemingly innocuous expansions. The alkali content of cement, which is not specified in this test, has been shown to largely affect expansion results. Furthermore the water-cement ratio has been shown to influence the amount of ASR expansion observed. The C227 does not have a specified water-cement ratio and as a result a wide range of expansion results can be observed using a single aggregates source.

The ASTM C289 is a test method covering the chemical determination of the potential reactivity of an aggregate with alkalis in cement. The test setup consists of crushing aggregates to a passing 300-μm sieve and retained on 150-μm sieve size and then exposing them to a 1 N sodium hydroxide solution at a temperature of 80° C. for a 24 hour period. After the aggregate is immersed for 24 hours the solution is then filtered and analyzed for the content of dissolved silica and the amount of alkalinity consumed. These two parameters are then plotted on a standard graph with regions defined for innocuous, deleterious, and potentially reactive behavior. Many aggregates are not accurately identified using this test method. A substantial number of well-known ASR reactive aggregates have been shown to pass this test while many innocuous aggregates are identified as deleterious. The interference of certain minerals, such as calcium, magnesium, silicates, gypson, zeolites, clay minerals, organic matter, or iron oxides, have been shown to cause erroneous results. Concrete aggregate gradation and proportioning in mixture design has been shown to strongly influence ASR expansion. For this reason the crushing and preparation of aggregates in this test has been criticized as a significant source of error because aggregate sizes used in typical concrete mix designs are not well represented.

The ASTM C1260 is a test method which permits the detection within 16 days of the potential of an aggregate in mortar bars to develop deleterious ASR expansion. The test is has been proven to be especially useful for aggregates that react slowly or produce expansion late in the reaction. The ASR reaction is accelerated by exposing mortar bars to a 1N sodium hydroxide solution which is kept at 80° C. The alkaline soaking solution provides the mortar bars with essentially and 'unlimited' supply of hydroxides in order to accelerate the reaction. This test is considerably valuable because it provides a rapid means of evaluating potentially reactive aggregates for use in concrete. However, this test method has been reported by many researchers as very severe and it has been shown in the past to identify aggregates as reactive that have good long-term service records. Furthermore, recently a group of aggregates shown to be innocuous using the ASTM C1260 developed substantial ASR related damage in the field. In general the ASTM C1260 is commonly used in conjunction with other criteria in order to establish whether an aggregate is suitable or not.

The ASTM C1293 is a test method that is used to determine, through the measurement of length change of concrete prisms, the susceptibility of a sample of an aggregate for participation in expansive ASR. Commonly referred to as "The Concrete Prism Test" (CPT), this method was developed in order to overcome the failure of the ASTM C227 to accurately identify aggregates subject to ASR. Much like the ASTM C1260 this test does not duplicate field conditions and as such actual field behavior of aggregates subject to ASR may not be well represented. It is therefore important that the ASTM C1293 be used as a criterion, in conjunction with other practices, to evaluate reactivity of aggregates. Nevertheless the ASTM C1293 has been shown to provide the best correlation with actual field performance and is currently regarded as the most authoritative test for evaluating aggregates for ASR.

Current methods used for assessing concrete damage in a field structure mainly rely on visual inspections performed at regular intervals. These inspections provide critical information on the structure condition; however, this information is rather qualitative and it strongly depends on the experience and skill of the inspectors. Furthermore, only the exterior body is inspected. Coring is then usually required. Several tests, such as compressive strength, can be conducted on cores but their sensitivity and reliability regarding ASR may vary significantly. In fact, there is no universal procedure to assess and quantify damage associated with ASR.

The limitations associated with existing laboratory tests prove that an ideal or all-encompassing method for predicting ASR reactivity of aggregates does not currently exist. More comprehensive investigation of test methods and the mechanisms that cause ASR induced expansion is required in order to develop a singular approach to identifying the susceptibility of aggregates for ASR reactivity. Presently the best means of preventing deleterious ASR, with great certainty, is to select aggregates that have good long-term service records. However, this is not always possible due to regional availability of aggregates. In addition, current condition assessment methods for existing concrete structures that may be subject to ASR are primarily limited to visual inspections or destructive testing methods. Visual inspection gives only information related to the surface condition of concrete and in some cases, such as NPPs, visual inspection or coring is highly prohibitive. Therefore, there is a need for an efficient non-destructive testing (NDT) method to monitor the progression of ASR in concrete structures.

Introduction to Acoustic Emission Monitoring

Acoustic emission is founded upon the phenomena whereby acoustic waves are released as energy from elastic or plastic deformations occurring within a material. ASTM E1316 (2006) defines acoustic emission (AE) as "the class of phenomena whereby transient elastic waves are generated by the rapid release of energy from localized sources within a material, or the transient elastic waves so generated". Propagation of AE waves can result from various sources including dislocations, micro-cracking, and other changes due to an increase in the strain. The method is very sensitive (within the ultrasonic frequency range) which provides the capability of detecting damage long before it is visible. Other advantages include real-time capability and the location damage regions. AE sensors capture and record the vibration of elastic stress waves as they reach the surface of a material. An AE sensor consists of piezoelectric crystal housed in aluminum or steel casing to protect it from damage. The piezoelectric crystal converts acoustic wave to an electric signal. Because changes in pressure on the surface of the material are usually miniscule the change in voltage is also very small. As a result amplification (internally or using external pre-amplifier) is necessary. Once amplified the signal is sent it to the data acquisition system. FIG. 1 shows a schematic for AE monitoring process.

Two common sensors are used in practice: resonant sensors and wide band (also known as broad band) sensors. Resonant sensors are sensitive to only a small range of frequencies thereby filtering out most of the frequency content. The resonant sensor is often chosen to give maximum sensitivity while minimizing unwanted background noise. Broadband sensors have nearly the same sensitivity over a wide range of frequencies thereby allowing for a frequency spectrum analysis. Due to wide range of frequencies captured by the broad band sensor it can be difficult to identify genuine AE from nonrelevant data and it is therefore generally a less sensitive sensor than a properly selected resonant sensor.

The passive ability of AE, external excitation or stimulus is not required for data collection once sensors are placed, makes it a suitable candidate for real-time monitoring and structural health monitoring of in-service structures. Numerous investigations were conducted to AE as a non-destructive evaluation (NDE) method for RC and PC structures, which are the main components of infrastructure such as highway bridges. The main challenge in these studies was wave attenuation and reflections due to the heterogeneous nature of concrete.

SUMMARY

Objects and advantages of the invention will be set forth in part in the following description, or may be obvious from the description, or may be learned through practice of the invention.

Methods are generally provided that can include, in one embodiment, monitoring a concrete structure using an acoustic emission sensor; detecting a defect formed in the concrete structure from the acoustic emission sensor; assessing any alkali-silica reaction within the concrete structure; and performing a alkali-silica reaction mitigation repair.

Other features and aspects of the present invention are discussed in greater detail below.

BRIEF DESCRIPTION OF THE DRAWINGS

A full and enabling disclosure of the present invention, including the best mode thereof to one skilled in the art, is set forth more particularly in the remainder of the specification, which includes reference to the accompanying figures, in which.

DETAILED DESCRIPTION

Figure 1:
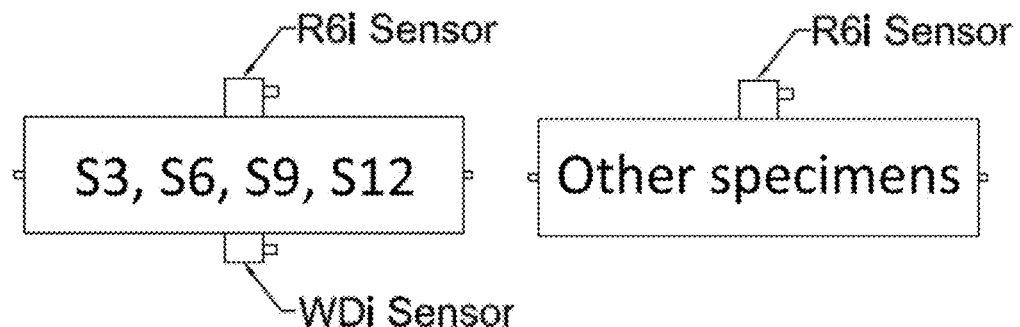
FIG. 1 shows an exemplary schematic for AE sensor layout.

Reference now will be made to the embodiments of the invention, one or more examples of which are set forth below. Each example is provided by way of an explanation of the invention, not as a limitation of the invention. In fact, it will be apparent to those skilled in the art that various modifications and variations can be made in the invention without departing from the scope or spirit of the invention. For instance, features illustrated or described as one embodiment can be used on another embodiment to yield still a further embodiment. Thus, it is intended that the present invention cover such modifications and variations as come within the scope of the appended claims and their equivalents. It is to be understood by one of ordinary skill in the art that the present discussion is a description of exemplary embodiments only, and is not intended as limiting the broader aspects of the present invention, which broader aspects are embodied exemplary constructions.

The present disclosure is generally directed to a method of acoustic emission (AE) as a condition assessment technique for alkali-silica reaction (ASR) in concrete. ASR is a chemical reaction occurring between alkaline hydroxides within cement past and certain types of amorphous silica found in mineral aggregates. ASR causes an accumulation of internal pressure due to the formation of a hygroscopic gel which leads to expansion and cracking of the concrete. AE is highly sensitive to stress waves emitted from a sudden release of energy such as formation of cracks in concrete. This allows it to capture and identify propagating damage. AE has the potential to detect micro-cracks forming prior to expansion, which can be related to the degree of ASR damage.

Thus, non-intrusive methods are generally provided for the detection and classification of alkali-silica reaction in concrete structures. Practical applications include monitoring of building, highway bridges, nuclear power plants, hydraulic structures for early damage detection and condition assessment.

In one embodiment, an algorithm is provided for the detection and classification of alkali-silica reaction in concrete structures. This method is the first and only non-intrusive method that is used for this particular application, and therefore can replace current state of the art which includes taking cores from the concrete structures which may not be feasible in some cases (such as in concrete containment structure in nuclear power plants).

I. The Alkali-Silica Reaction Mechanisms

Despite being studied so heavily some aspects of the mechanisms causing ASR expansion and cracking are not well understood. In general for ASR to occur three conditions must exist: a high alkaline environment, reactive silica, and moisture.

Reactive silica commonly occurring in various types of minerals reacts with hydroxyl ions present in pore solution of cement matrix. The silica now dissolved in pore fluid is available to react with sodium ($Na^+$) and potassium ($K^+$) alkalis. The reaction causes the formation of a volumetrically unstable hygroscopic alkali silica gel. For the sake of simplicity the reaction can be schematically represented as the following:

Step 1

Silica+alkali→alkali-silica gel(sodium silicate)

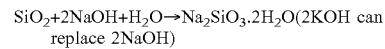

$SiO_2 + 2NaOH + H_2O \rightarrow Na_2SiO_3 \cdot 2H_2O$ (2KOH can replace 2NaOH)

Step 2

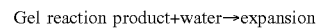

Gel reaction product+water→expansion

Once the alkali silicate gel is hydrated it begins to expand and causes the development of internal stresses within the cement matrix and surrounding aggregates. Expansive pressure continues to accumulate as the bulky alkali silicate gel absorbs water until the tensile limit of the concrete is exceeded. Micro-cracking ensues leading to additional ingress and absorption of water, additional gel formation, and eventually failure of the concrete occurs.

Silica (silicon oxide tetrahedron) can be found in many commonly occurring natural aggregates. The silicon tetrahedron consists of 4 oxygen ions ($O^{2-}$) bonded to a single silicon ion ($Si^{4+}$) located in the center of the structure. A crystalline network is formed in three-dimensional space by the repetition of the silicon tetrahedron. Each oxygen ion is bonded to two silicon ions in order to achieve electrical neutrality. The chemical bonding in crystalline silica shows the ordered regularity of a lattice, whereas non-crystalline silica has more the appearance of a random network.

Complete tetrahedra cannot form at the surface of the crystalline structure, and therefore bonds between oxygen and silicon are broken resulting in charges that are unsatisfied. Regardless crystalline silica structures are chemically and mechanically stable, impermeable, are only reactive at the surface. Non-crystalline or amorphous silicates are formed when the linking of tetrahedral is random forming a structure that is much more porous and has much larger surface areas. As a result amorphous silica is very reactive. The crystalline structure of silicates is formed when melted silica cools and hardens. The rate of cooling strongly influences the forming of crystals. Rapidly cooled silicates are often non-crystalline to some extent. In general the more amorphous the silica is the more reactive it becomes.

Another factor influencing the ASR reactivity is the amount of energy stored in the crystalline structure of an aggregate. Various silica structures through heat and pressure may develop large amounts of stored strain energy. Many ASR prone aggregates contain these types of silicates. However these aggregates react with alkaline hydroxides at a much slower rate than that of amorphous silicates. Metamorphic aggregates containing strained quartz are an example of such aggregates. Additionally some crystalline silicates, such as chert, contain very fine crystals with very large surface areas and as such are very prone to ASR.

Two conditions that have also been proven to influence ASR induced expansion are the size and proportion of reactive aggregates. A certain proportion of some reactive siliceous aggregate causes the largest expansion in concrete, and the expansion decreased when the content of reactive aggregate in the concrete was increased or decreased from that pessimum proportion. It is also know that ASR induced expansion was largest at a certain grain size for a given proportion of reactive aggregate and expansion decreased when the grain size was increased or decreased from that pessimum size.

II. Method of Detection

This study reports the results of acoustic emission monitoring for detection of ASR degradation in concrete specimens. The findings of this study can be summarized as follows:

Acoustic emission can detect ASR damage. Continual AE activity was recorded from the specimens conditioned for one year, which shows that formation of microcracks and ASR by-products do not inhibit collection of AE data.

The rate of AE activity can be related to the rate of ASR degradation. This can help evaluate the efficiency of ASR mitigation strategies by comparing the rate of AE activity before and after the repair for a prescribed duration.

An acoustic emission Intensity Analysis chart for ASR damage classification was proposed by correlating AE results with petrographic examination (DRI measurements). This chart can be used for health monitoring to enable proper identification of the extent of ASR damage. More data is needed to validate the proposed limits and extend the chart to include heavy ASR damage.

EXAMPLES

An accelerated ASR test (modified ASTM C1293) was designed to enable detection of ASR expansion in a reasonable time frame. The specimens were continuously monitored using AE. Expansion measurements were performed periodically using a length comparator along with petrographic examination to serve as a benchmark for ASR detection. The objective of the research was to use AE to assess the development and rate of ASR distress in concrete for use in service life modeling. The results of the test showed the ability of AE to detect ASR progression with a good agreement with length change measurements. The results of petrographic examination of the specimens are to be reported on in the future.

The experimental setup included an adapted ASTM C1293 test, twelve specimens of dimensions 3×3×11.25 in. created using a highly reactive aggregate as well as an elevated alkaline content, and 3 control specimens of similar dimensions incorporating innocuous aggregates and low-alkaline cement. The specimens were placed in controlled environment with high temperature and relative humidity to accelerate the ASR reaction. Length change measurements and petrographic examination were performed periodically to detect ASR damage while AE activity was recorded continuously. The results of this study show that AE has the ability to detect ASR damage with a good agreement with length change measurements. Furthermore, AE cumulative signal strength can be related to the length expansion associated with ASR distress and the intensity analysis chart has the potential to classify ASR damage in concrete structures.

I. INTRODUCTION

Alkali-silica reaction (ASR) is one of the primary chemical reactions causing degradation and loss of service of hardened concrete structures worldwide. ASR is reaction that occurs over time in concrete between aqueous alkaline hydroxides, within the pore solution of the cement paste ($Na_2O$ and $K_2O$), and amorphous silica, within surrounding aggregates. The accumulation of expansive pressure created by the hydrated alkali silicate leads to micro-crack formation within both the cement paste and aggregates. If left unchecked ASR can cause extensive map-cracking, spalling of joints, excessive movements, and ultimately loss of service and safety of a structure.

Currently the most popular method of preventing ASR related damage to concrete structures is proper selection of aggregates. This can be achieved through field performance assessment of a potential aggregate but aggregates with satisfactory long-term service records are not always regionally available. A number of various test methods have been developed to evaluate the potential of an aggregate to participate in expansive ASR. However, current testing methods have limitations. The two most prevalent standard test methods being used currently are the ASTM C1293 ("Concrete Prism Test") and the ASTM C1260 ("Accelerated Mortar Bar Test"). Both test methods have, in some cases, falsely identified aggregates as innocuous resulting in ASR related damage of in-place structures. For these reasons it is necessary to conduct field assessments in order to evaluate the condition of the structure.

Regular inspections are needed to determine the extent and rate of ASR deterioration. Visual inspection, however, only gives information related to the surface condition of concrete. Therefore, there is a need for an efficient non-destructive testing (NDT) method to monitor the progression of ASR. The lack of a NDT method that is able to detect ASR is a crucial issue, especially with the wide implementation of concrete in NPPs structures and the threat that radioactive leaking imposes. Excessive cracking in such elements might lead to compromising the ability of these structures to fulfill their intended functions. The NDT technique should enable (1) proper assessment of the rate of ASR deterioration and (2) evaluate the remaining service life of the structure. Acoustic emission (AE) methods have advanced significantly in the past years as a real-time, passive NDT technique for evaluating damage in concrete structures. These advancements pave the way for developing a quantitative method for evaluating ASR. AE is highly sensitive to stress waves emitted from sudden release of energy, such as concrete cracks. This allows it to capture and identify propagating damage. Possible applications of AE monitoring related to the progression of ASR include long-term monitoring and prognosis based on received AE data using parameter based methods.

An accelerated ASR test based upon the ASTM C1293 was designed to enable detection of ASR expansion in a reasonable time frame. The specimens were continuously monitored using AE. Length change measurements were performed periodically using a length comparator along with petrographic examination to serve as a benchmark for ASR detection. The objective of the research is to use AE to assess the development and rate of ASR distress in concrete for use in service life modeling. The results of the test showed the ability of AE to detect ASR progression with a good agreement with length change measurements.

II. EXPERIMENTAL PROGRAM

The test matrix included four sets of three for a total of twelve specimens with dimensions of 3×3×11.25 in., according to ASTM C1293, in addition to three dummy specimens of the same dimensions. The primary difference between this test setup and ASTM C1293 is the alkalinity concentration where 5% $Na_2O_{(Eq)}$ was used in the concrete mix as opposed to 1.25% as specified in the ASTM standard. Also, due to the significantly shortened time frame of this test, a more frequent length change measurement schedule than that of the ASTM C1293 was incorporated.

In addition to higher total alkaline content a highly reactive aggregate originating from Cheyenne, Wyo., known as Knife River, was used for casting the test specimens. Typically in order evaluate the potential for a coarse aggregate to participate in deleterious ASR a known innocuous fine aggregate would be used as per ASTM C1293. However, for the purposes of this testing (significant ASR expansion desired) both the coarse and fine aggregates were used from the same source and are considered highly reactive. With this exception the aggregates follow the specifications identified in section 7.2 of ASTM C1293. A highly reactive aggregate was chosen in conjunction with elevating total alkaline content in order to ensure that an alkali-silica reaction would occur and that AE data related to expansive ASR damage could be captured within a reasonable period of time.

The specimens were placed in a controlled environment with a 100% relative humidity and temperature of 100±2° F. A sealed insulating chamber was constructed to control the temperature. The chamber has approximate dimensions of 4×4×8 ft and consists of an aluminum frame covered with Lexan panels. In order to create a temperature stable environment a silicon adhesive sealant was applied to corners and seams and expanding polyurethane foam was used in areas where cables were routed into the chamber. A small electric heater with an internal fan was placed inside the chamber and temperature was controlled by a digital thermostat mounted on the wall outside the chamber.

To maintain 100% relative humidity, specimens were placed in polyethylene containers with sealing lids conforming to the specifications identified in section 5.2.2 of the ASTM C1293. The containers were lined with a polypropylene absorbent fabric. A specimen holder consisting of a bottom rack, central rod, and top plate was placed inside of each bucket.

The purpose of the specimen holder assembly is to provide a means for the secure upright storage of each specimen. The specimen holder consists of materials that are chemically inert in high moisture environments. The bottom rack and top plate is made of PVC plastic and the central rod is machined from a high-grade stainless steel, which is an important consideration because the capability of AE to detect corrosion in materials has been shown. If any of the materials inside of the storage buckets are subject to corrosion there is a potential for data being captured that is unrelated to ASR damage.

A single hole was cut in the side of each container to allow access for the AE sensor cables. Once sensor cables were routed into the containers these holes were sealed using rubber grommets and an adhesive silicon sealant. The containers were filled with tap water up to a depth of approximately 1 in. to maintain a relative humidity of 100%.

The specimens are situated above the surface of the reservoir of water by resting on the bottom rack of the specimen holder assembly. The specimens were maintained in this position and were kept out of contact with the sides of the container. Each container housed 3 individual specimens, yielding a total of four containers.

The containers were rested on a 2.5×3.5 ft platform that consisted of two layers of ¾ in. rigid foam insulation and a single piece of ½ in. plywood. The electric heater was positioned at the far side of the chamber was placed on a similar platform. The platforms were provided in an attempt to create a buffer for the instrumented specimens and thus minimize collection of noisy or nonrelevant AE data originating from vibrations in the concrete floor below.

A. Concrete Materials and Mixture Design

Concrete prisms used for testing have mixture proportions (cement, water, coarse aggregate) designed using the specifications identified in the ASTM C1293. Two batches of concrete were used for making specimens both having the same mixture design and each batch yielding 6 specimens for a total of 12 specimens. Specimens from 'Batch 1' are labeled S1 through S6 while specimens from 'Batch 2' are labeled S7 through S12. The dummy specimens were cast prior to testing and contained aggregates and cement that are known to behave innocuously; they are labeled as D1 through D3.

The ASTM C1293 specifications and concrete mixture design are shown in Tables 1 and 2. The control specimens were selected from laboratory specimens previously cast that contained aggregates that are known to be innocuous.

TABLE 1

ASTM C1293 Section 7.3 specifications

| | |
|---|---|
| w/c Ratio* = | 0.45 |
| Cement Content = | 26.22 lb/ft$^3$ |
| Volume of Coarse Aggregate per Unit Volume of Concrete = | 0.70 |
| **Alkali Content = | 5.0% Na$_2$O$_{eq}$ |

*Based upon aggregate saturated surface dry
**Modified from ASTM C1293 (1.25% Na$_2$O$_{(Eq)}$)

TABLE 2

Concrete mixture design
Modified ASTM C1293 Mix Design: One Batch of 6 Prisms V$_{tot}$ = 0.3515 ft$^3$

| Constituent | Weight (lb) | S.G. | Volume (ft$^3$) | Mix Proportion- Mass Basis (%) | Mix Proportion- Volumetric Air-Free Basis (%) |
|---|---|---|---|---|---|
| Cement | 9.2090 | 3.150 | 0.0469 | 17.4 | 13.2 |
| Water | 4.438 | 1.000 | 0.0711 | 8.4 | 20.0 |
| Coarse Aggregate | 24.160 | 2.662 | 0.1454 | 45.7 | 40.8 |
| Fine Aggregate | 14.561 | 2.629 | 0.0888 | 27.5 | 24.9 |
| NaOH Admixture | 0.535 | 2.131 | 0.0040 | 1.0 | 1.1 |
| Total | 52.903 | — | 0.3562 | 100.0 | 100.0 |

The coarse and fine aggregate originate from a quarry in Cheyenne, Wyo. and are known to be highly reactive. The properties of the aggregates are shown below in Table 3. The specific gravity (S.G.) and absorption were measured by The Wyoming Department of Transportation Materials Lab (Table 3). The unit weight of the coarse aggregate was measured at the University of Wyoming using ASTM C29 methodology and is also shown in (Table 3). The properties shown in Table 3 were used to proportion the concrete mix as per the ASTM C1293 specifications. The grain size distribution of each aggregate (conforming to ASTM C1293) is shown in Table 4. The fine aggregate was sieved and proportioned such that a fineness modulus of 2.75 was achieved. Laboratory grade sodium hydroxide (NaOH) pellets were used to increase the alkalinity of the concrete.

TABLE 3

Knife River aggregate properties

| Knife River | S.G. | Unit Weight (lb/ft$^3$) | Absorption (%) |
|---|---|---|---|
| Coarse Aggregate | 2.662 | 98.8 | 0.67 |
| Fine Aggregate | 2.629 | — | 0.91 |

A Type I ordinary Portland cement was used in the mix design and was generously provided by Holcim Cement. The cement was analyzed in accordance with the ASTM C114 and the cement alkaline content was measured as 0.509% Na$_2$O equivalent. The ASTM C1293 specifies the use of cement having a minimum of 0.90% Na$_2$O equivalent. However, due to the nature of this test and material availability the lower cement alkaline content was considered reasonable.

TABLE 4

Concrete aggregate size distribution

| Aggregate | Size (U.S. Standard) | Percent Passing | Percent Retained | Cumulative Percent Retained |
|---|---|---|---|---|
| Coarse | 3/4" | 100 | 0 | 0 |
| | 1/2" | 66.7 | 33.3 | 33.3 |
| | 3/8" | 33.3 | 33.3 | 66.6 |
| | 1/4" | 0 | 33.3 | 100 |
| Fine | No. 4 | 100 | 0 | 0 |
| | No. 8 | 90 | 10 | 10 |
| | No. 16 | 75 | 15 | 25 |
| | No. 30 | 40 | 35 | 60 |
| | No. 50 | 20 | 20 | 80 |
| | No. 100 | 0 | 20 | 100 |
| | Pan | 0 | 0 | — |

B. Casting and Instrumentation Program

Concrete used for casting specimens was mixed according to the ASTM C192. A mechanical pail batch mixer was used and the mixing procedure (based on ASTM C192 7.1.2 'Machine Mixing') can be summarized as the following:

1. Dissolve the NaOH pellets in the cool mixing water
2. Add some of the water and coarse aggregate prior to rotation of mixer
3. Start the mixer
4. Add the remaining coarse aggregate, fine aggregate, cement, and water
5. Continue mixing for 3 minutes after all materials have been incorporated
6. Stop the mixer for 3 minutes of rest and cover the opening with plastic
7. Uncover the opening and mix for an additional 2 minutes.
8. Place the mixture in a clean mixing pan.

After the mixture was moved to a clean mixing pan, fresh mixture characteristics and air content tests were performed. Concrete slump was measured per ASTM C143 and immediately following unit weight (bulk density) and yield tests were performed using ASTM C138 methodology. Air content was measured using the ASTM C231 pressure method. The fresh mix characteristics for both batches used in the casting of specimens is shown in Table 5. After testing the concrete was returned to the mixing pan and specimens were cast according to ASTM C157 standards.

TABLE 5

Fresh mix characteristics

| Mix | Slump (in) | Unit Weight (lb/ft$^3$) | Air Content (%) | Relative Yield |
|---|---|---|---|---|
| Batch 1 | 2.5 | 145.3 | 1.7 | 1.02 |
| Batch 2 | 2.5 | 144.1 | 1.8 | 1.03 |

The casting of specimens consisted of filling each mold with concrete up to approximately 1/2 of its depth and tamping 25 times evenly across the cross-section of the mold and then slightly overfilling and tamping an additional 25 times evenly across the cross-section of the mold.

After the top layer was compacted excess concrete was struck off flush with the top surface of the mold and the top surface was trowel finished. The molds were covered with polyethylene plastic and allowed to set undisturbed for a 24 hour period.

One batch of 6 specimens was cast and allowed to set for a 24 hour period. Immediately after 24 hours the first batch of specimens was demolded and initial comparatory length measurements were recorded. Acoustic emission sensors were then affixed to the specimens using a two part epoxy (ASTM E1316) and each specimen was subsequently placed in a container for storage. Once the first batch of specimens was properly stored acoustic emission data acquisition was started. Immediately after the first batch of specimens were stored and monitored, the second batch of specimens will be cast and handled using the same methodology as the first batch.

The surface of each specimen was lightly roughened, then cleaned, and the sensors were attached using a standard two part epoxy (ASTM E1316 2006). The sensors were affixed only to sides of the prisms that were in contact with the steel mold in order to promote a clean couple between the surface of the specimen and the AE sensor. However, after two weeks of testing the coupling between the sensors and some of the specimens was weakened due to the high temperature and humidity. Therefore, a two part epoxy manufactured specifically for these conditions was used to re-attach the sensors and no subsequent coupling issues were encountered.

The instrumented specimens were placed in each storage container immediately after the epoxy was allowed to set and cure. The coaxial sensor cables are fitted with a male-to-female connector which allows for the cables to be readily removed from the AE sensors.

C. Length Change Measurements

Length change measurements were taken at 1, 7, 10, 14, 21, 28, and 56 days using a Humboldt length comparator equipped with a digital display dial gauge. Each time the specimens were removed for length change measurements the AE data acquisition system was stopped before hand and then measurements were taken. Five readings were recorded for each specimen and the average of those readings was reported. After length change readings were recorded the specimens were returned to storage containers and pencil lead breaks were performed (ASTME1316) in order to ensure the AE sensors were still firmly coupled with the specimens. After pencil lead breaks were performed the containers and chamber were closed and the temperature was allowed to recover for a period of approximately one hour. This was done in order to minimize any noise in the AE data associated with thermal expansion of specimens or materials in contact with the specimens.

The subsequent comparator readings were compared to the initial comparator reading to determine the length change percentage. The comparator readings were taken per ASTM C157. However, due to the nature of this research program, specifically the AE instrumentation involved, the subsequent comparator readings were not taken in conformance with Section 10.2.2 of ASTM C1293. The process of soaking the specimens for 16 hours in a moist cabinet was omitted from the measurement procedure in order to minimize the time required to measure the specimens. This is an important consideration because AE data was not collected during the process of taking length change readings. The specimens were, therefore, removed from their storage containers and measured immediately for length change. The length change measurement procedure can be summarized as the follows:

1) Stop AE data acquisition;
2) Open containment chamber;
3) Open a storage container, remove a single specimen, replace container lid;
4) Close containment chamber;
5) Take length change readings;
6) Place measured specimen aside, repeat steps 2-5 for all specimens in the batch;
7) Return all specimens to storage containers;
8) Perform pencil lead breaks;
9) Replace container lids, close chamber, allow temperature to recover for 1 hour; and
10) Restart AE data acquisition.

The concrete prisms are rotated in the comparator and a length change reading is taken while the specimen is spinning. The length change measurements are very small (on the order of 0.0001 in.), and it is imperative for the spinning procedure to be as consistent as possible. For this reason counter weights of similar dimension and weight were machined from stainless steel and affixed to the specimens. The counter weights were located opposite the position of the AE sensors, in order to balance the center of mass of the concrete prism. Erratic 'wobbling' of specimens during spinning and length change readings may result in noisy length change results.

The ASTM C 1293 sets forth an expansion limit of 0.04% after one year of testing as the threshold for identifying an aggregate as potentially susceptible to deleterious ASR expansion. This criterion was used as a benchmark for the presence and extent of ASR damage occurring in each specimen.

D. Petrographic Examination

Three specimens were scheduled to be removed for petrographic examination after 14, 28, and 56 days in order to verify the presence of ASR in conjunction with length change measurement. These specimens were selected at random.

Petrographic examination is a destructive testing method that can assess damage in concrete by visual inspection of concrete slices, usually extracted from concrete cores, under a microscope. Petrographic examination was conducted at the Wiss, Janney, Elstner Associates, Inc., Austin office (WJE-Austin) using a Damage Rating Index (DRI) procedure. This method is used in Europe and Canada to semi-quantitatively define distress in concrete due to ASR. The Federal Highway Administration (FHWA) references this procedure in their published manual on concrete petrography. DRI is estimated by measuring certain features and multiplying each of them by a correspondent weighting factor. There are many versions of the DRI method, differing mainly in the assignment of weighting factors. WJE has modified the method to include deterioration in the fine aggregate in the rating index. The modified distress features and the corresponding weighting factors, adopted from FHWA, are shown in Table 5.1.

TABLE 5.1

ASR Damage Rating Index Features and Weighting Factors

| Distress Feature | Weighting Factor |
| --- | --- |
| Cracks in either coarse or fine aggregate (CAgg) | 0.25 |
| Cracks and gel in coarse or fine aggregate (C + GAgg) | 2.0 |
| Aggregate debonded (DAgg) | 3.0 |
| Reaction rims around aggregate (RR) | 0.5 |
| Cracks in cement paste (CCP) | 2.0 |
| Cracks and gel in cement paste (C + GCP) | 4.0 |
| Air voids with gel (GAV) | 0.5 |

The samples were prepared as for a typical petrographic examination, including curing and lapping. After the samples are lapped, the following two steps were taken:

A 1-cm square transparency grid was overlaid on the lapped concrete surface. The transparency was trimmed to the size of the sample and securely taped to the concrete so that it will not move during examination.

The stereomicroscope was set to a magnification of 16× and a ring light was used to achieve uniform lighting. The magnification was adjusted as necessary to better assess the distress; however, all DRI measurements were done at 16× for consistency.

The DRI was then calculated by moving across the sample and tallying each occurrence of each feature in each 1-cm square and multiplying the tally for each feature with its weighting factor. A final DRI value is then obtained by averaging the results of all the 1-cm squares examined and multiplying by 100.

E. Acoustic Emission Monitoring

AE is defined as transient stress waves emitted from sudden release of energy, such as crack initiation or growth [ASTM E1316 2013]. Each AE signal is called a 'hit' and is associated with a waveform that can be used to calculate different parameters such as amplitude, duration, rise time, absolute energy, and signal strength, along with different frequency parameters. Two types of sensors were used to monitor AE activity in the specimens. One 55 kHz resonant AE sensor having 40 dB integral pre-amplification (R6i) was used on each specimen and placed at the mid-length of the specimen. The Sensor Highway II System (SHII) manufactured by Mistras Group was used for continuous AE monitoring of the specimens. This system is equipped with 16 high-speed channels and 16 parametric input channels. It is rated for outdoor use and comes housed in a rugged weather proof enclosure. The SHII system is connected to a desk top computer and data collection and processing is achieved through Physical Acoustics Corporation's AEwin software. AEwin is a data acquisition and replay program capable of graphing identified hits/events and waveforms as well as source location and detailed event analysis. AEwin was used to process and filter AE data collected during experimentation.

All the specimens were instrumented with one 55 kHz resonant AE sensor having a 40 dB integral pre-amplification (R6i) placed at the centerline of the longitudinal face of the specimen. Four of the specimens were also instrumented with a broad band AE sensor (WDi). This study only focuses on the data from the resonant sensors. Data collection threshold was set for amplitude of 40 dB. Each storage container housed one specimen being monitored by both a R6i and a WDi sensor and the remaining two specimens being monitored with a R6i alone. FIG. 1 shows schematic for AE sensor layout.

The data collection threshold was set at 40 dB. AE data was recorded continuously during the test except for the short pauses where length measurements were taken.

F. Data Acquisition Schedule

The test setup includes petrographic analysis of the specimens periodically to serve as a benchmark for the progression and extent of ASR damage. Three specimens each were removed at 14, 28, and 56 days and shipped to WJE in Austin, Tex. for petrographic examination. A total of 9 specimens have been tested and sent for petrographic investigation. At the time of this thesis the remaining 3 specimens are still being tested along with the dummy specimens. The results of the petrographic analysis have not yet been reported. The results of petrography and length change and AE data for the 3 remaining test specimens, being monitored up to one year, will be reported on in the future.

III. RESULTS

This section discusses length change measurements and AE results for 5 ASR specimens as well as the 3 control specimens. Of the 5 ASR specimens discussed 2 were removed at 56 days for petrographic examination and the other 3 are still being tested but results up to 56 days for these specimens is presented. The control specimens were monitored for AE activity for a period of 42 days following the removal of the first 3 ASR specimens after 14 days of testing.

A. AE Data Filtering

Amplitude duration and signal strength parameters were used in AE data filtration and analysis. AE data filtering is an essential step to remove data not pertinent to the test. A baseline AE was recorded by placing AE sensors on control specimens to check the noise levels in the environmentally controlled chamber. This test showed that mechanical and electrical noise were generally minimal. Given the small cross-section of the specimens, and since no loading was applied, the irrelevant AE data will be primarily from wave reflections. Therefore, a duration-amplitude filter (D-A) was used to reject AE data related to reflection, also known as Swansong II filter. The filter was determined through visual inspection of AE waveforms. The filter limits are shown in Table 6.

TABLE 6

AE data rejection limits for D-A filter

| Rejection Limits | | Rejection Limits | |
| --- | --- | --- | --- |
| Amp (dB) | Duration (μs) | Amp (dB) | Duration (μs) |
| 40-44 | 400 | 61-65 | 1,000 |
| 45-48 | 500 | 66-70 | 1,500 |
| 47-52 | 600 | 71-75 | 2,500 |
| 53-56 | 700 | 76-80 | 3,500 |
| 57-60 | 800 | 91-95 | 5,000 |

B. AE Results Versus Length Change Measurements

The results of the filtered AE data in comparison with length change measurements are presented in this section. The initial comparator reading was considered as the zero point for length change measurement (approximately 24 hours after casting). A line is shown at day 14 on each plot showing AE and length change percentage results. This line marks the point at which the AE sensors were reattached to the specimens using epoxy which is more suitable for high temperature and humidity conditions. The results from the filtered AE data collected from the 3 control specimens are also shown in this section for comparison with the test specimens. Control specimens D1, D2, and D3 were monitored for 42 days following the removal of the first 3 test specimens for petrographic analysis at day 14.

Figure 2:
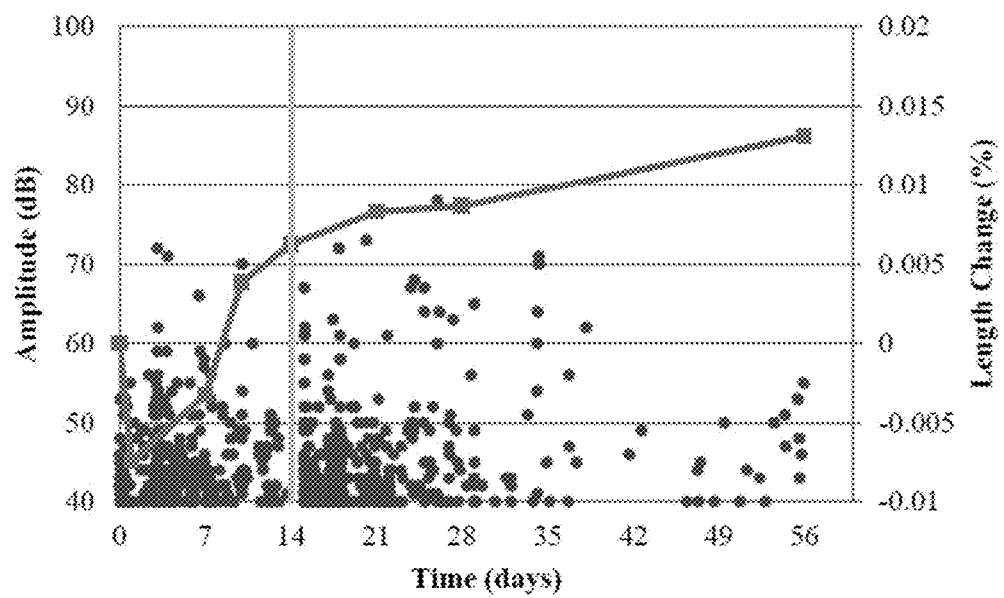
FIG. 2 shows AE data in terms of amplitude and length change with respect to time for test specimen S3 of the Examples.

After 56 days of testing, no visible signs of cracking were observed on the surface of the ASR specimen S3, although significant staining of the specimen was present. FIG. 2 shows AE data in terms of amplitude and length change with respect to time for test specimen S3. The first length change reading at 1 day shows a decrease in the length of the specimen which is attributed to shrinkage. Following this measurement the length change steadily increases to a maximum value of 0.013% at 56 days (approximately 33% of the threshold specified by the ASTM C1293 for potentially deleterious aggregates after one year). A marked increase in AE activity can be seen after 14 days. This is due to the deterioration of the original epoxy during the first 14 days of testing which resulted in weakening of couple between the AE sensor and the specimen. The poor coupling attributed to the diminished sensitive of the AE sensors during the first 14 days.

Figure 3:
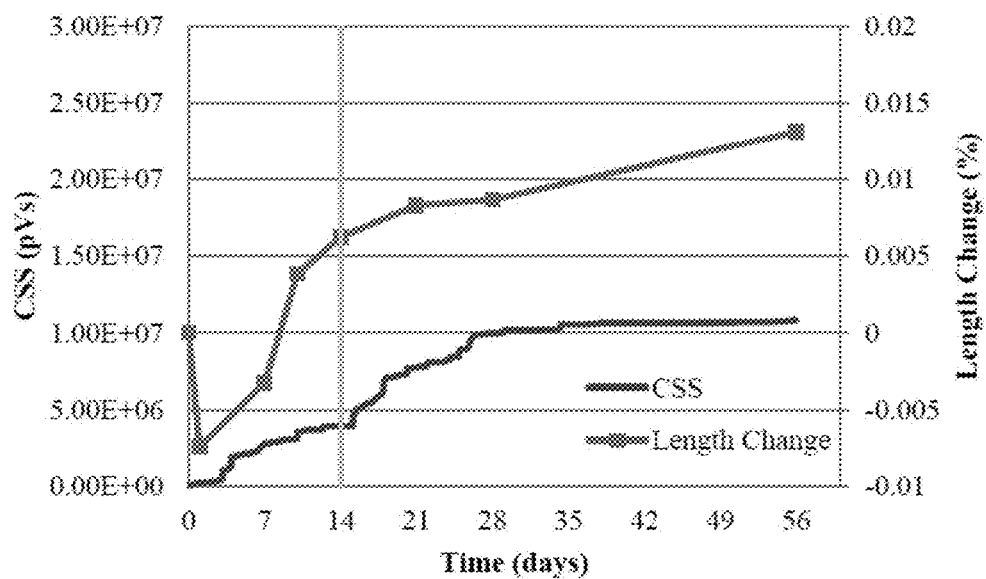
FIG. 3 shows the cumulative signal strength (CSS) of AE signals and length change with respect to time for specimen S3 of the Examples.

FIG. 3 shows the cumulative signal strength (CSS) of AE signals and length change with respect to time for specimen S3. CSS graphs are used to give a better indication regarding the degree of degradation in the structure. In this case, an increase in the CSS can be attributed to cracks forming as a result of ASR expansion. As seen in the figure, CSS did not increase significantly during the first 3 days of the test. A significant increase in the rate of CSS was then detected until 28 days. This increase matches the increase in the expansion detected from length change measurements. It is noted that AE has the ability to detect the formation of micro-cracks in real-time. In ASR tests, formations of cracks will precede significant changes in the length measurements; therefore, a behavior such as that shown in FIG. 3 is expected (high rise in AE activity followed by expansion). The rate of CSS decreased afterwards indicating that fewer cracks are forming during this time (between 28 and 56 days). At the time of this thesis specimen S3 is still being monitored and is scheduled to be tested for a one year period.

Figure 4:
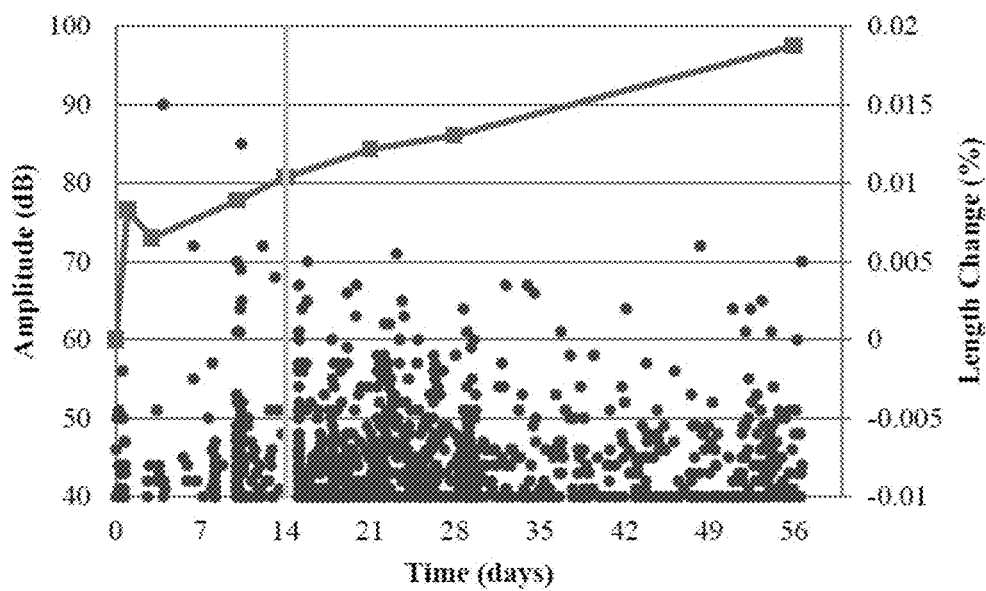
FIG. 4 shows AE data, in terms of amplitude, and length change with respect to time for test specimen S5 of the Examples.

The surface of the ASR specimen S5 was significantly stained. FIG. 4 shows AE data, in terms of amplitude, and length change with respect to time for test specimen S5. Specimen S5 showed the highest amount of AE activity and as expected it also exhibited the largest expansion (0.019%) of all the specimens monitored for 56 days. A small decrease in length is shown during the first week of testing this is potentially a result of operator error associated with length change measurement. Again a marked increase in AE activity can be observed after 14 days; this is attributed to the better coupling of the moisture resistant epoxy.

Figure 5:
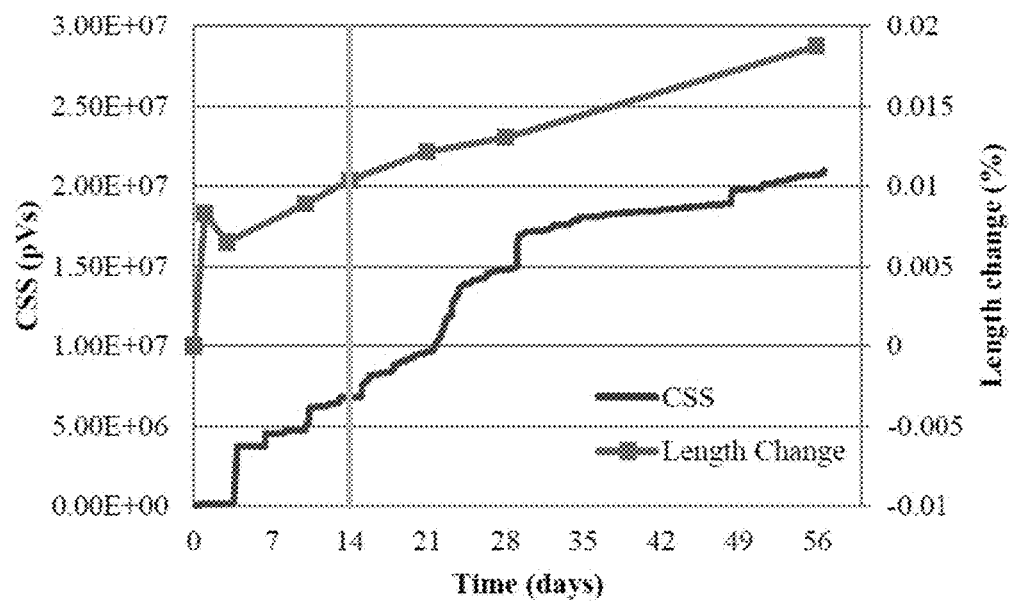
FIG. 5 shows the CSS of AE signals and length change with respect to time for specimen S5 of the Examples.

FIG. 5 shows the CSS of AE signals and length change with respect to time for specimen S5. CSS did not increase significantly during the first 4 days of the test. A relatively steady increase in the rate of CSS was then detected until around up to 56 days. This increase matches well with the increase in the expansion detected from length change measurements. Specimen S5 shows a substantial amount of AE activity continuing to occur up to the 56 day point which indicates that a significant amount of ASR related cracking continues to occur also. This is expected as the rate of length increase steadily increases after the first week up to 56 days. A marked spike in CSS can be observed around day 4 of testing. This increase corresponds well with expansion shown in length change measurements and is attributed to the beginning of significant crack nucleation due to ASR. In general CSS agrees well with measured length change. This indicates that expansive crack formation is captured effectively by acoustic emission. Specimen S5 shows continued AE activity after 56 days. At the time of this thesis Specimen S5 is still being monitored and is scheduled to be tested for a one year period.

Figure 6:
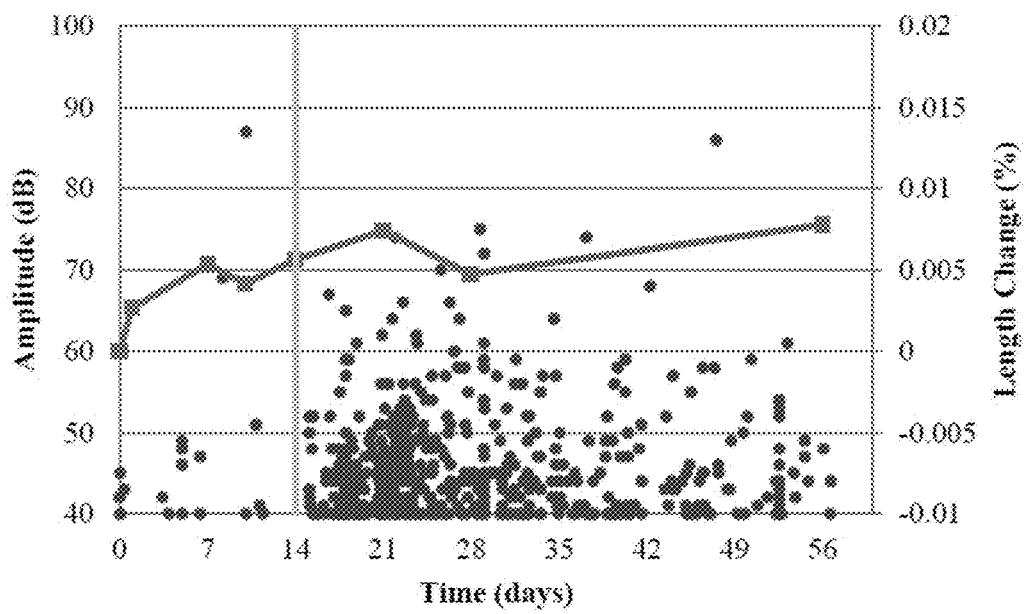
FIG. 6 shows amplitude and length change with respect to time for test specimen S6 of the Examples.

ASR specimen S6 also showed deep staining at the surface. FIG. 6 shows amplitude and length change with respect to time for test specimen S6. Specimen S6 showed an expansion of 0.008% after 56 days of testing. Although this expansion is slightly less than that of the other test specimens it still accounts for 20% of the 0.04% limit, specified by ASTM C1293 at one year, after only 2 months of testing. Decreases in length were measured in two instances and these are perceived to be related to operator error associated with the length comparator readings. A poor coupling due to the deterioration of the first epoxy used to attach the AE sensors resulted in very little AE hits occurring during the first 14 days of testing.

Figure 7:
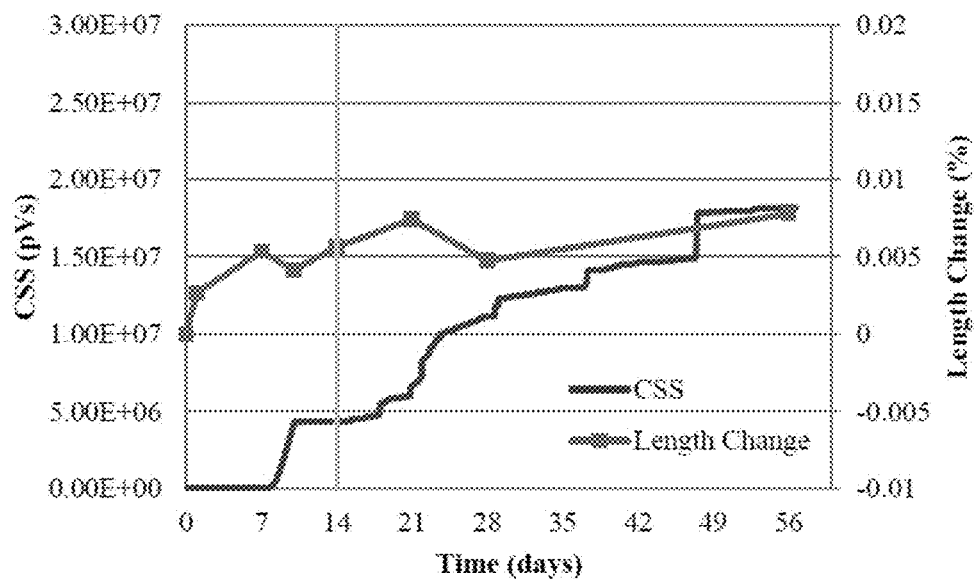
FIG. 7 shows the CSS of AE signals and length change with respect to time for specimen S6 of the Examples.

FIG. 7 shows the CSS of AE signals and length change with respect to time for specimen S6. A clear and steady increase in in CSS is observed after 14 days up to day 56 of testing. Other than a spike around day 10 very little AE is observed in the first 14 days of testing. The sharp rise in CSS at day 10 is considered noise resulting from the deterioration of the original epoxy used to attach the AE sensors. In general the trend in CSS agrees well with length change measurements.

Figure 8:
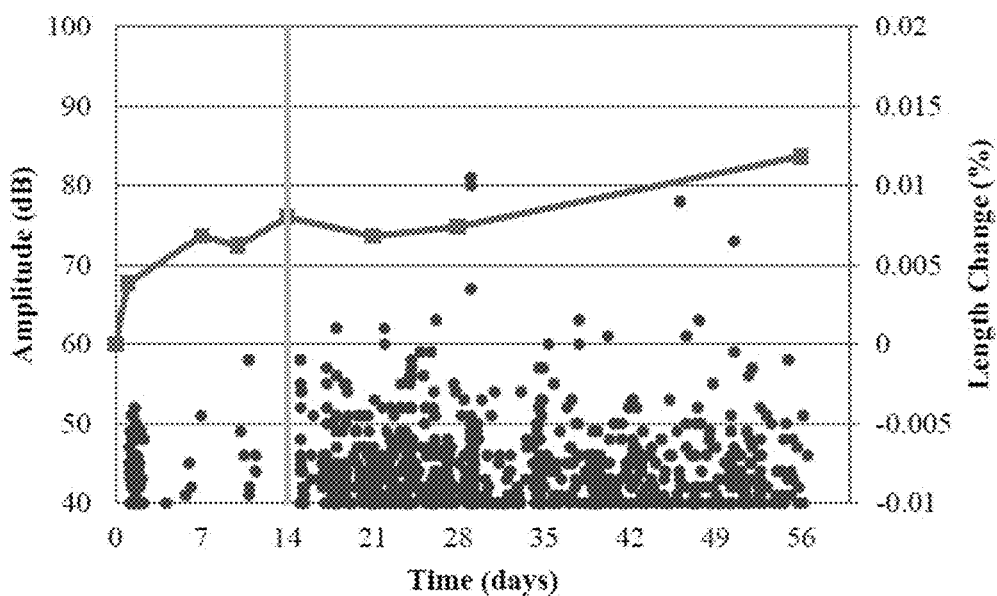
FIG. 8 shows amplitude and length change with respect to time.

As with other ASR specimens S10 showed marked staining at the surface. Amplitude and length change with respect to time is shown in FIG. 8. Specimen S10 increased in length by 0.012% at 56 days. Due to the weakened couple between the AE sensor and the specimen a limited number of AE hits were recorded during the first 14 days of testing. However, from 14 days up to day 56 a significant number of events were recorded. Some decreases in length were measured on days 10 and 21. These decreases are small (less than 0.0025%) and are attributed to operator error associated with the length comparator. In general the length change measurements agree well with the AE data. Specimen S10 remained very active up to day 56 and is scheduled to be monitored for a one year period.

Figure 9:
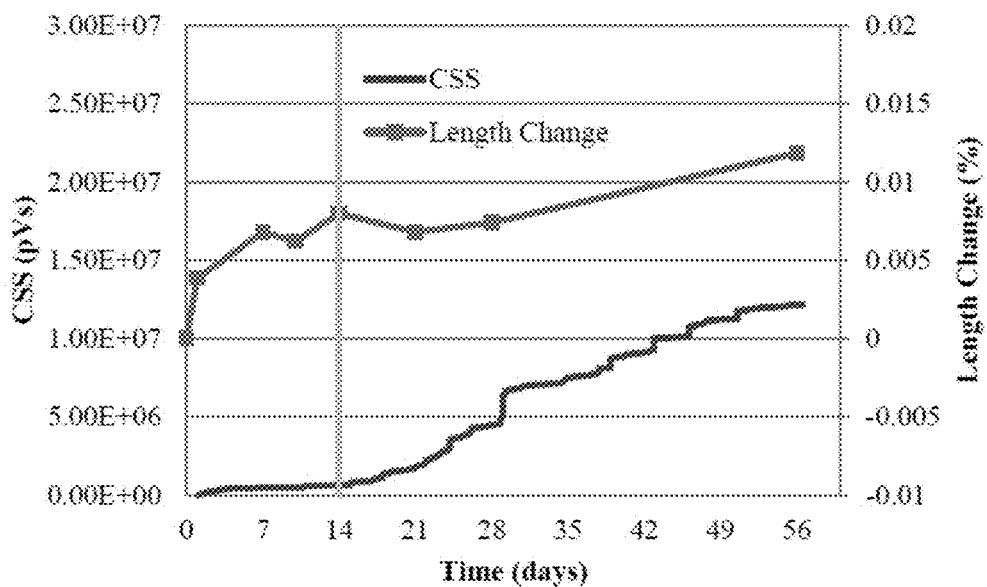
FIG. 9 shows the CSS of AE signals and length change with respect to time for specimen S10 of the Examples.

FIG. 9 shows the CSS of AE signals and length change with respect to time for specimen S10. A steady increase in CSS is shown from day 14 up to day 56 which corresponds with the steady increase in length that was measured. As crack formation progresses both expansion and CSS are expected to increase which is the case for specimen S10. Again, very little CSS due to AE activity was observed during the first 14 days of testing. This is attributed to the deterioration of the first epoxy used to attach AE sensors which compromised the couple between the sensor and specimen.

Figure 10:
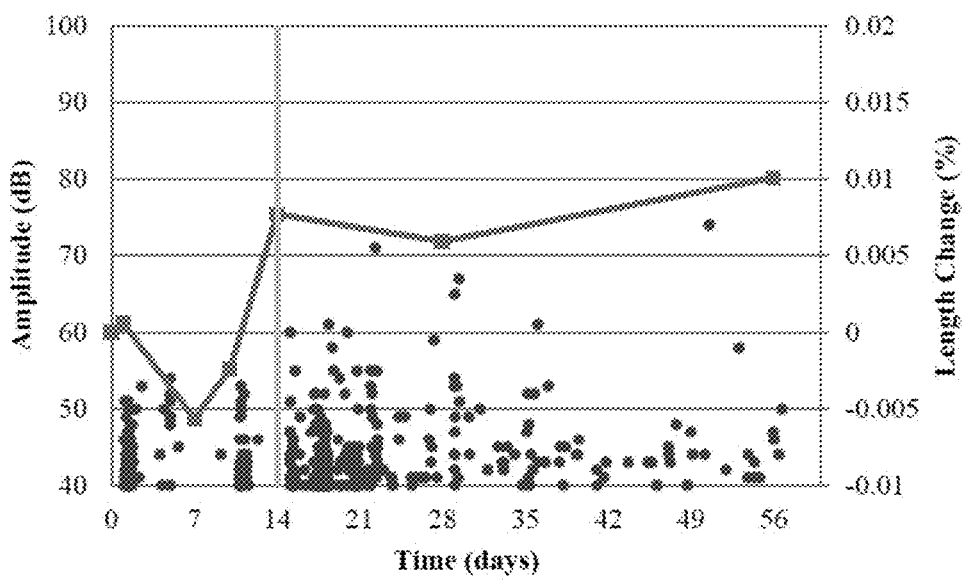
FIG. 10 shows amplitude and length change with respect to time for test specimen S12 of the Examples.

Like the other test specimens significant staining was present on the surface of the ASR specimen S12. FIG. 10 shows amplitude and length change with respect to time for test specimen S12. An expansion of 0.010% was measured for specimen S12 (25% of threshold ASTM C1293 for deleterious aggregates) after 56 days of testing. Some decrease in length was measured during first week and this is attributed to shrinkage. Overall a general trend of increasing length was observed which corresponds well with AE activity. Like the other specimens a limited amount of AE was collected during the first 14 days due to the problems associated with the deterioration of epoxy used to attach the AE sensors to the specimens. The figure shows that a decrease of AE activity was detected towards the end of the test. This was attributed to a dominant period in crack growth which follows the formation of the initial cracks within the aggregates and the formation of expansive ASR gel.

Figure 11:
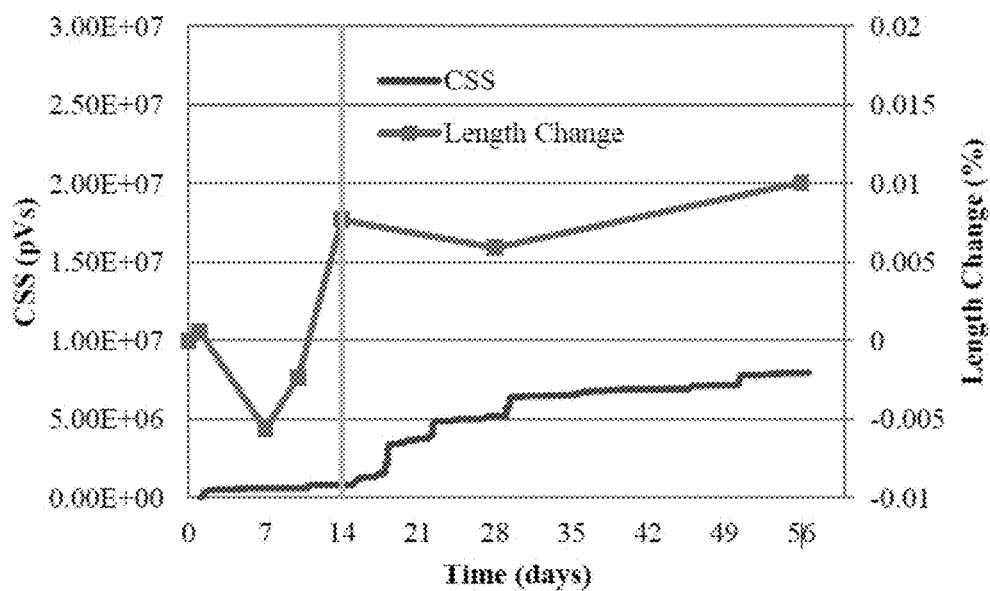
FIG. 11 shows the CSS of AE signals and length change with respect to time for specimen S12 of the Examples.

FIG. 11 shows the CSS of AE signals and length change with respect to time for specimen S12. In general a trend of increasing CSS corresponds with the overall increase in length that was measured for the specimen. A small decrease in length was measured at day 28. This is attributed to operator error associated with the length comparator readings.

Figure 12:
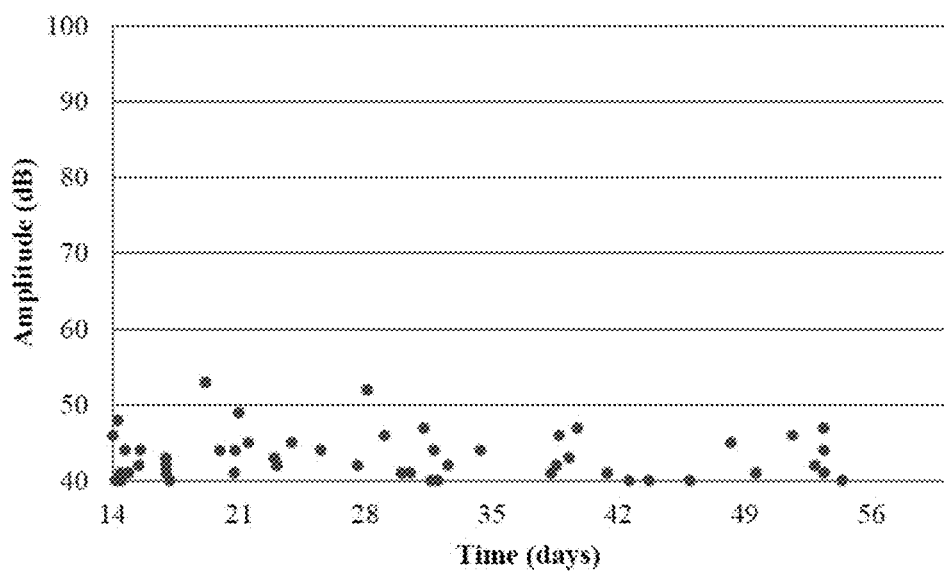
FIG. 12 shows amplitude with respect to time for control specimen D1 of the Examples.

No staining appeared on at the surface of the control specimen D1 after 42 days of testing as with the ASR specimens. FIG. 12 shows amplitude with respect to time for control specimen D1. The figure shows that very little AE hits were recorded for control specimen D1 in comparison with all of the other test specimens. It should be noted that, due to the highly sensitive nature of AE, even with proper filtering techniques it is impossible to remove all noise and nonrelevant information from the AE data set. The hits shown in FIG. 12 are either caused by noise or are a result of phenomena unrelated to ASR induced expansion and cracking.

Figure 13:
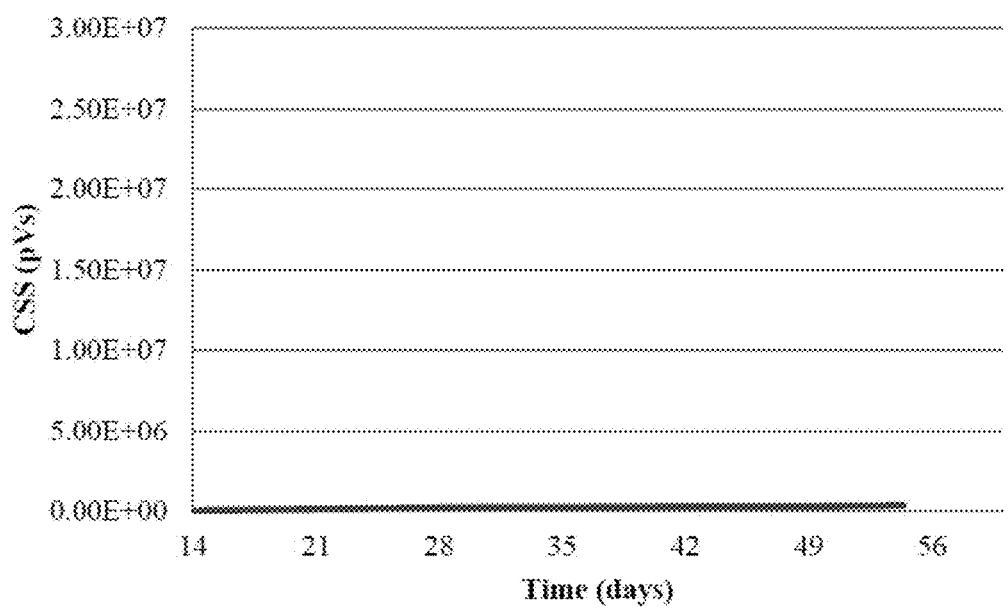
FIG. 13 shows the CSS of AE signals with respect to time for control specimen D1 of the Examples.

FIG. 13 shows the CSS of AE signals with respect to time for control specimen D1. The figure shows that the increase in CSS during the 42 days AE data was collected was negligible. The minimal amount of hits recorded and the resulting insignificant CSS for control specimen D1 can be attributed to the fact that no crack formation is occurring within the specimens due to ASR.

Figure 14:
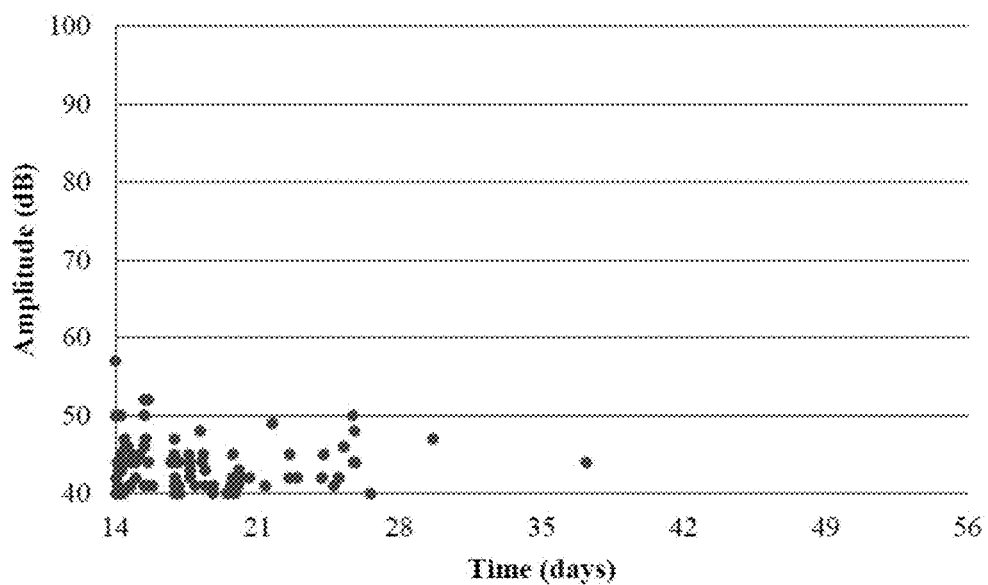
FIG. 14 shows the amplitude with respect to time for control specimen D2 of the Examples.

No staining was observed on the surface of the Control specimen D2. FIG. 14 shows the amplitude with respect to time for control specimen D2. The figure shows that in general the number of AE hits recorded was much less than that of the ASR specimens. The majority of the AE hits occur during the first 28 days of monitoring. Inspection of the AE waveforms associated with the individual hits confirms that these signals are primarily a result of noise or other mechanisms that are unrelated to ASR deterioration.

Figure 15:
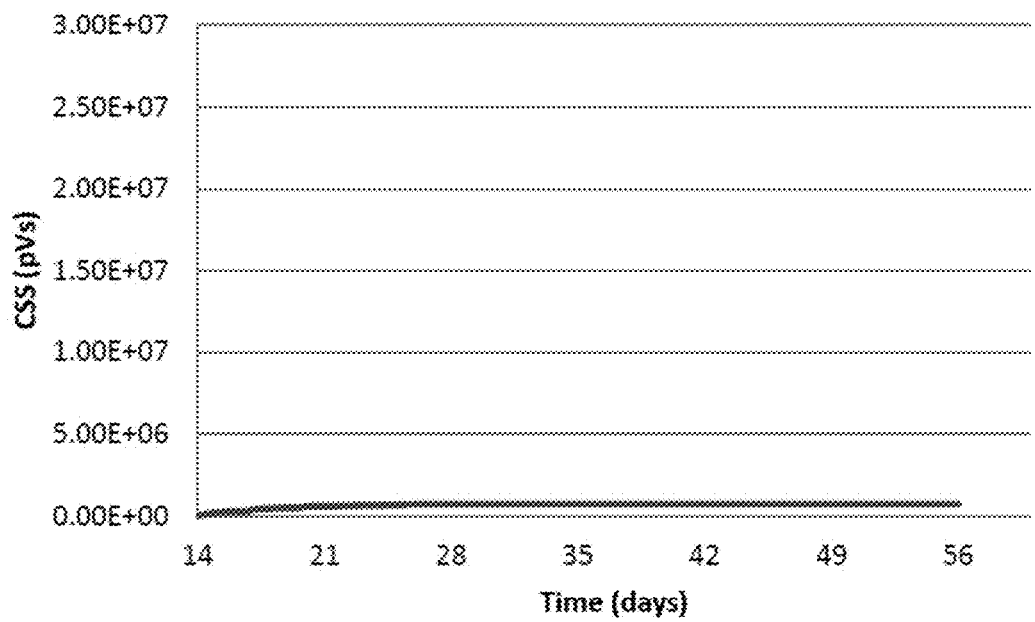
FIG. 15 shows the CSS of AE signals with respect to time for control specimen D2 of the Examples.

FIG. 15 shows the CSS of AE signals with respect to time for control specimen D2. The figure shows that CSS is negligible compared to the ASR specimens. After day 28 CSS is essentially constant. This indicates that no cracking or release of energy is occurring within the specimen related to ASR. This behavior is expected because the control specimens contain low-alkaline cement and innocuous aggregates.

Figure 16:
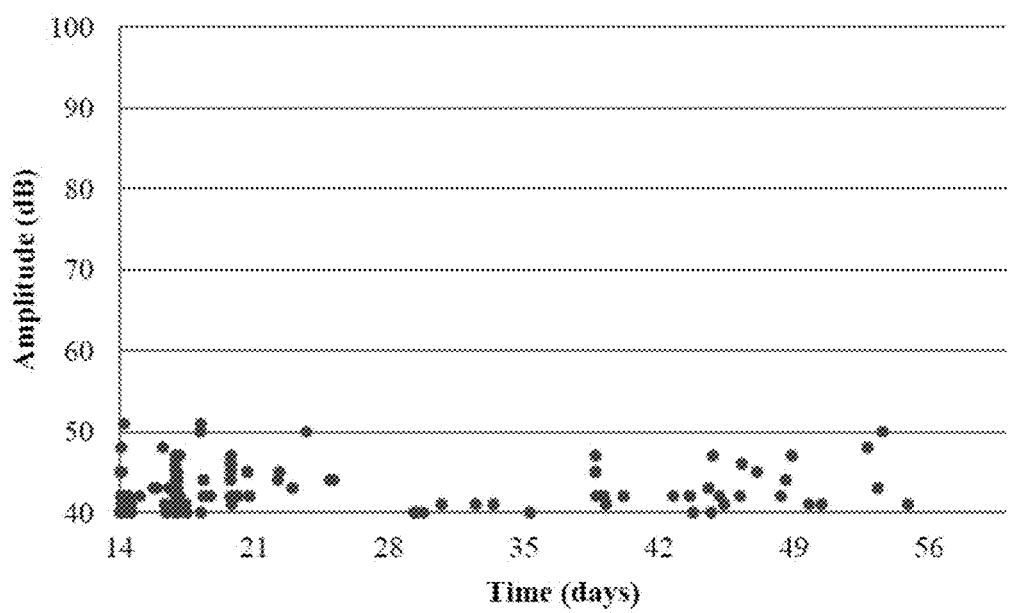
FIG. 16 shows the amplitude with respect to time for control specimen D3 of the Examples.

The Control specimen D3 showed no staining on the surface. FIG. 16 shows the amplitude with respect to time for control specimen D3. The number of hits shown in the figure is much less than that of the test specimens. Inspection of the waveforms associated with these hits indicates that they are primarily caused by noise or irrelevant sources.

Figure 17:
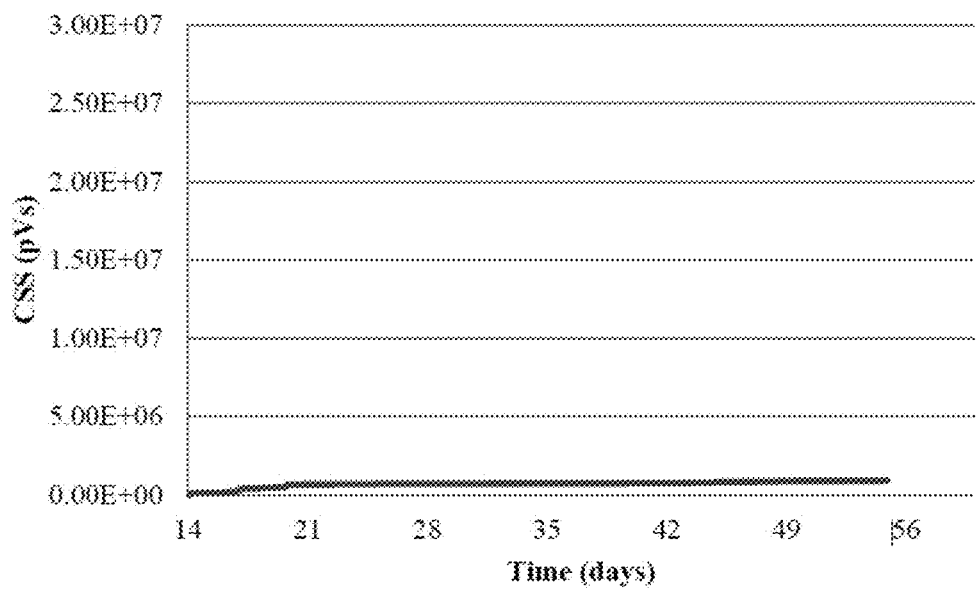
FIG. 17 shows the CSS of AE signals with respect to time for control specimen D3 of the Examples.

FIG. 17 shows the CSS of AE signals with respect to time for control specimen D3. The figure shows that control specimen D3 experienced a negligible increase in CSS during monitoring. Like the other dummy specimens this behavior expected for innocuous behavior of the aggregates. The insignificant level of AE activity indicates that no ASR induced expansive cracking is occurring in the specimen.

A summary of the maximum length change of each of the ASR specimens along with maximum CSS value (test and dummy specimens) is reported in Table 7. Length change at 56 days of the ASR specimens ranges from 0.008% to 0.019%. After 56 days of testing, length change values range from around 20% to 50% of the limit value (after one year of testing) specified by ASTM C1293 for identifying aggregates as potentially deleterious. S6 has the least length change percentage and specimen S12 has the least CSS value. In general the value of length change percentage and CSS are comparable between the test specimens. The control specimens were not measured for length change but they contain cement and aggregates that are known to behave innocuously and therefore negligible length change is anticipated for these specimens. The CSS values for the control specimens are in general 2 orders of magnitude less than that of the test specimens. This illustrates the potential of CSS as an indication of ASR damage. However, CSS can only be used as an indication based on the rate of change because assigning numerical values with such parameters will be highly influenced by the specimen size and AE attenuation, which changes even in very similar specimens.

TABLE 7

Length change measurements and AE data

| Specimen Number | Length Change (%) | Cumulative Signal Strength (pVs) |
|---|---|---|
| S3 | 0.013 | $1.08 \times 10^7$ |
| S5 | 0.019 | $2.10 \times 10^7$ |
| S6 | 0.008 | $1.82 \times 10^7$ |
| S10 | 0.012 | $1.21 \times 10^7$ |
| S12 | 0.010 | $7.94 \times 10^6$ |
| Dummy 1 | — | $3.68 \times 10^5$ |
| Dummy 2 | — | $7.52 \times 10^5$ |
| Dummy 3 | — | $9.13 \times 10^5$ |

C. AE Intensity Analysis Versus Length Change Measurements

AE intensity analysis was used to provide a better assessment of ASR damage. This approach was initially developed to assess damage in fiber reinforced polymer vessels (Fowler et al 1989). Recently, intensity analysis was used to quantify damage mechanisms in quantify concrete structures such as corrosion (ElBatanouny et al. 2011). The method uses the signal strength (SS) to calculate two parameters; historic index and severity. Historic index, H(t), estimates the change in the slope of the CSS in historic approach while severity, Sr, is the average signal strength of the largest 50 hits. Historic index and severity can be calculated using Eq. (1) and Eq. (2) where: N is number of hits up to a time (t), Soi is the signal strength of the i-th event, and K is empirically derived factor that varies with number of hits. In this study, the value of K was selected to be: a) N/A if $N \leq 50$, b) $K=N-30$ if $51 \leq N \leq 200$, c) $K=0.85N$ if $201 \leq N \leq 500$, and d) $K=N-75$ is $N \geq 501$.

$$H(t) = \frac{N}{N-K} \frac{\sum_{i=K+1}^{N} S_{oi}}{\sum_{i=1}^{N} S_{oi}} \quad (1)$$

$$S_r = \frac{1}{50} \sum_{i=1}^{i=50} S_{oi} \quad (2)$$

Figure 18:
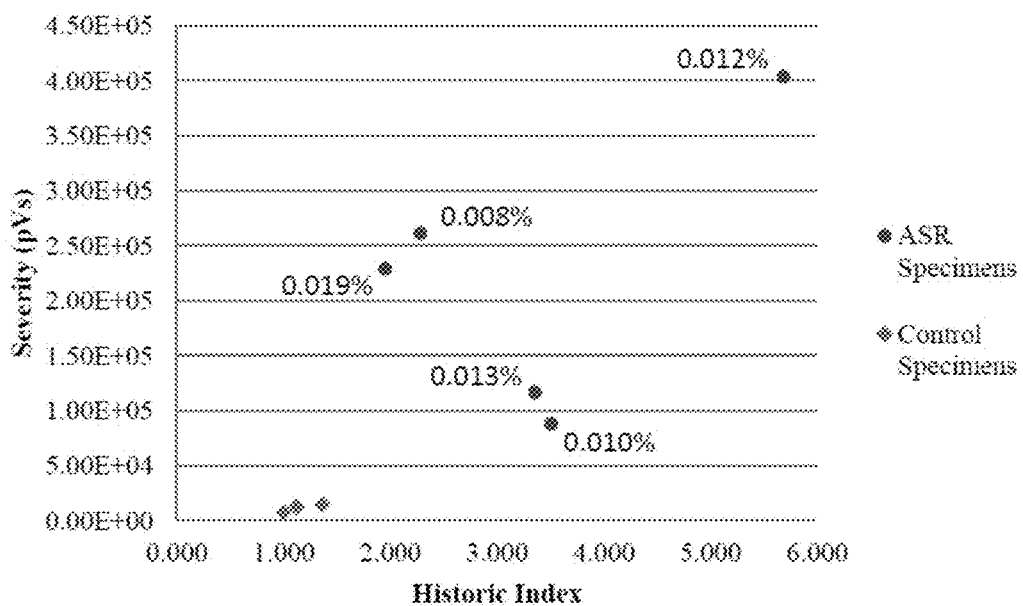
FIG. 18 shows the intensity analysis results for the ASR specimens (length change % on each data point) and the 3 control specimens.

The intensity analysis chart is obtained by plotting the maximum severity and historic index acquired during the test where the points plotted to the top-right corner of the figure indicates more damage. FIG. 18 shows the intensity analysis results for the ASR specimens (length change % on each data point) and the 3 control specimens. As seen in the figure, the control specimen data plots towards the bottom-left corner of the figure while the data from the ASR specimens plot towards the top-right corner. With more data, empirical boundaries classifying ASR damage levels can be established which enables the quantification of this damage mechanism in similar specimens.

IV. SUMMARY AND CONCLUSIONS

An accelerated alkali-silica reaction (ASR) test was designed to examine the ability of acoustic emission (AE) to detect this damage mechanism. ASR is a chemical reaction occurring between alkaline hydroxides from the cement past and certain types of amorphous silica within mineral aggregates. ASR causes an accumulation of internal pressure due to the formation of an expansive gel which leads to swelling and cracking of concrete. AE is highly sensitive to stress waves emitted from sudden release of energy, such as formation of cracks in concrete. This allows it to capture and identify propagating damage. AE has the potential to detect micro-cracks forming prior to expansion, which can be related to the degree of ASR damage.

IV. ASR DAMAGE CLASSIFICATION

The specimens were placed in a controlled environment with high humidity and temperature to accelerate the reaction, while being continuously monitored with acoustic emission. Length change measurements and petrographic examination were conducted periodically to serve as benchmarks for ASR damage detection. Micro-cracking associated with ASR damage was detected by AE and the rate of AE activity was correlated to the rate of ASR damage. An AE based intensity analysis chart that enables ASR damage classification in correlation with petrographic analysis was developed.

The experimental setup consisted of an adapted ASTM C1293 test, twelve specimens of dimensions 3×3×11.25 in. created using a highly reactive aggregate as well as an elevated alkaline content, and 3 control specimens of similar dimensions incorporating innocuous aggregates and low-alkaline cement. The specimens were placed in controlled environment with high temperature and relative humidity to accelerate the ASR reaction. Length change measurements and petrographic examination were performed periodically to detect ASR damage while AE activity was recorded continuously.

The results of this study show that AE is able to detect ASR damage with a good agreement with length change measurements. The specimens containing reactive aggregate, along with elevated alkalinity show a general trend of increasing length which indicates the presence of ASR damage. The results of petrographic analysis have not yet been reported on, however, significant staining was observed on the surface of the ASR affected specimens. Staining and discoloration is often a precursor for ASR induced crack formation at the surface. AE cumulative signal strength also corresponded well with the length change associated with ASR damage. An AE intensity analysis was performed using severity and historic index parameters. The ASR distressed specimens plotted in the higher damage regions of the intensity analysis chart which demonstrates its viability for classification of ASR damage. This research program is ongoing and with the progress of testing, more data will be available which may help in the determination of damage level boundaries.

This study is intended to determine the feasibility of AE for condition assessment of structures subject to ASR deterioration. It is also important for the ASR damage assessment program to have the capability of distinguishing AE related to ASR distress as opposed to other mechanisms such as loading or thermal expansion/contraction.

These and other modifications and variations to the present invention may be practiced by those of ordinary skill in the art, without departing from the spirit and scope of the present invention, which is more particularly set forth in the appended claims. In addition, it should be understood the aspects of the various embodiments may be interchanged both in whole or in part. Furthermore, those of ordinary skill in the art will appreciate that the foregoing description is by way of example only, and is not intended to limit the invention so further described in the appended claims.

What is claimed:

1. A method of detection of alkali-silica reactions in a concrete structure comprising:
    monitoring the concrete structure using a resonant acoustic emission sensor; and
    detecting hits associated with cracking and expansion of the concrete structure resulting from the alkali-silica reactions using the resonant acoustic emission sensor; and
    assessing the cracking and expansion of the concrete structure resulting from the alkali-silica reactions by monitoring the hits.

2. The method of claim 1, wherein the defect is a micro-crack.

3. The method of claim 1, wherein the alkali-silica reactions form $Na_2SiO_3$.

4. The method of claim 1, wherein the alkali-silica reactions form $K_2SiO_3$.

5. The method of claim 1, wherein strength and rate of the hits are used to assess the concrete structure's cracking and expansion.

6. The method of claim 1, wherein the resonant acoustic emission sensor is a 55 kHz resonant emission sensor.

7. The method of claim 1, further comprising measuring a change in length of the concrete structure and using the change in length in assessing the concrete structure.

8. The method of claim 5, further comprising determining the cumulative signal strength by summing energy from each of the hits.

9. The method of claim 5, further comprising determining the cumulative signal strength by summing energy from each of the hits.

10. The method of claim 5, wherein the assessing the concrete structure further includes measuring temporal sequencing of the hits.

* * * * *